United States Patent
Steinle et al.

(10) Patent No.: US 12,201,373 B2
(45) Date of Patent: Jan. 21, 2025

(54) DETERMINING A CONFIGURATION OF A MEDICAL ROBOTIC ARM

(71) Applicant: Brainlab AG, Munich (DE)

(72) Inventors: Wolfgang Steinle, Munich (DE); Christoffer Hamilton, Aschheim (DE); Nils Frielinghaus, Heimstetten (DE)

(73) Assignee: Brainlab AG, Munich (DE)

( * ) Notice: Subject to any disclaimer, the term of this patent is extended or adjusted under 35 U.S.C. 154(b) by 7 days.

(21) Appl. No.: 15/563,825

(22) PCT Filed: Nov. 2, 2015

(86) PCT No.: PCT/EP2015/075427
§ 371 (c)(1),
(2) Date: Oct. 2, 2017

(87) PCT Pub. No.: WO2017/028935
PCT Pub. Date: Feb. 23, 2017

(65) Prior Publication Data
US 2018/0085175 A1    Mar. 29, 2018

(30) Foreign Application Priority Data

Aug. 19, 2015 (WO) ................ PCT/EP2015/069037
Sep. 3, 2015   (WO) ................ PCT/EP2015/070153

(51) Int. Cl.
*A61B 34/30*        (2016.01)
*A61B 34/10*        (2016.01)
(Continued)

(52) U.S. Cl.
CPC .............. *A61B 34/20* (2016.02); *A61B 34/10* (2016.02); *A61B 34/30* (2016.02); *A61B 90/37* (2016.02);
(Continued)

(58) Field of Classification Search
CPC ......... A61B 34/20; A61B 90/50; A61B 90/37; A61B 34/30; A61B 34/10;
(Continued)

(56) References Cited

U.S. PATENT DOCUMENTS 5,544,282 A * 8/1996 Chen ............... B25J 9/1666
700/255
7,176,795 B2 * 2/2007 Roed ................ H04B 5/02
340/568.1

(Continued)

FOREIGN PATENT DOCUMENTS

CN    104780849 B  * 11/2018  ............ A61B 34/10
CN    111670014 A  *  9/2020  ........... A61B 17/068
(Continued)

OTHER PUBLICATIONS

"Robot-assisted RF ablation with interactive planning and mixed reality guidance;" Rong Wen, Chin-Boon Chng, Chee-Kong Chui, Kah-Bin Lim, Sim-Heng Ong, Chang, S.K.-Y; 2012 IEEE/SICE International Symposium on System Integration (SII) (pp. 31-36); Dec. 1, 2012.*
(Continued)

*Primary Examiner* — Khoi H Tran
*Assistant Examiner* — Jorge O Peche
(74) *Attorney, Agent, or Firm* — Tucker Ellis LLP (57) ABSTRACT

A computer implemented method for determining a configuration of a medical robotic arm, wherein the configuration comprises a pose of the robotic arm and a position of a base of the robotic arm, comprising the steps of: acquiring treatment information data representing information about the treatment to be performed by use of the robotic arm; acquiring patient position data representing the position of a patient to be treated; and calculating the configuration from the treatment information data and the patient position data.

20 Claims, 4 Drawing Sheets

(51) Int. Cl.
*A61B 34/20* (2016.01)
*A61B 90/00* (2016.01)
*A61B 90/50* (2016.01)
*B25J 9/16* (2006.01)
*G06T 7/00* (2017.01)
*G06T 7/70* (2017.01)
*G06T 11/00* (2006.01)
*A61N 5/10* (2006.01)

(52) U.S. Cl.
CPC ............. *A61B 90/50* (2016.02); *B25J 9/1666* (2013.01); *B25J 9/1676* (2013.01); *G06T 7/0012* (2013.01); *G06T 7/70* (2017.01); *G06T 11/001* (2013.01); *A61B 2034/105* (2016.02); *A61B 2034/107* (2016.02); *A61B 2034/2055* (2016.02); *A61B 2090/364* (2016.02); *A61B 2090/365* (2016.02); *A61N 5/1049* (2013.01); *A61N 2005/1059* (2013.01); *G06T 2207/10024* (2013.01); *G06T 2207/10028* (2013.01); *G06T 2207/10081* (2013.01); *G06T 2207/10088* (2013.01); *G06T 2207/30024* (2013.01); *G06T 2207/30241* (2013.01)

(58) Field of Classification Search
CPC ...... A61B 2090/397; A61B 2034/2051; A61B 2034/2057; A61B 2034/2063; A61B 2090/3929; A61B 10/0233; A61B 2034/2068; A61B 2034/2059; A61B 2034/2055; A61B 2090/3979; A61B 2090/3975; A61B 2090/365; A61B 2034/107; A61B 2034/105; A61B 2090/0481; A61B 2090/364; G06T 7/0012; G06T 11/001; G06T 7/70; G06T 2207/10081; G06T 2207/10024; G06T 2207/10028; G06T 2207/30241; G06T 2207/10088; G06T 2207/30024; B25J 9/1666; B25J 9/1676; A61N 2005/1059; A61N 5/1049

See application file for complete search history.

(56) References Cited

U.S. PATENT DOCUMENTS

| | | | | |
|---|---|---|---|---|
| 7,723,057 B1 * | 5/2010 | Snow | ................ | G01N 33/6896 435/7.1 |
| 8,571,710 B2 * | 10/2013 | Coste-Maniere | ...... | B25J 9/1671 606/130 |
| 9,956,042 B2 * | 5/2018 | Simaan | ................ | A61B 34/74 |
| 10,394,327 B2 * | 8/2019 | Chizeck | ................ | G06T 7/97 |
| 10,740,866 B2 * | 8/2020 | Katouzian | ............. | G06V 20/62 |
| 11,141,859 B2 * | 10/2021 | Steinle | ................ | A61B 34/30 |
| 11,642,182 B2 * | 5/2023 | Ecke | ................ | G16H 40/63 600/476 |
| 2001/0013764 A1 * | 8/2001 | Blumenkranz | ........ | A61B 34/37 318/568.11 |
| 2003/0050527 A1 * | 3/2003 | Fox | ................ | A61N 2/006 600/13 |
| 2003/0083903 A1 * | 5/2003 | Myers | ................ | G16H 15/00 705/2 |
| 2003/0109780 A1 * | 6/2003 | Coste-Maniere | ..... | G06T 7/0012 600/407 |
| 2003/0236476 A1 * | 12/2003 | Inman | ................ | A61H 23/0263 601/101 |
| 2005/0159987 A1 * | 7/2005 | Rosenfeld | ................ | G16H 70/60 600/300 |
| 2005/0177400 A1 * | 8/2005 | Rosenfeld | ................ | G16H 50/20 705/3 |
| 2005/0223176 A1 * | 10/2005 | Peters, II | ................ | B25J 13/00 711/141 |
| 2006/0241718 A1 * | 10/2006 | Tyler | ................ | G06F 3/015 607/45 |
| 2007/0250119 A1 * | 10/2007 | Tyler | ................ | A61N 1/36103 607/2 |
| 2008/0009772 A1 * | 1/2008 | Tyler | ................ | G06F 3/015 600/595 |
| 2009/0089081 A1 * | 4/2009 | Haddad | ................ | G16H 20/40 705/2 |
| 2009/0177081 A1 * | 7/2009 | Joskowicz | ............. | A61B 90/36 606/130 |
| 2009/0183740 A1 * | 7/2009 | Sheffer | ................ | A61B 34/20 606/103 |
| 2009/0271035 A1 * | 10/2009 | Lurz | ................ | B25J 9/1664 700/245 |
| 2009/0306741 A1 * | 12/2009 | Hogle | ................ | A61N 1/36103 600/595 |
| 2009/0312817 A1 * | 12/2009 | Hogle | ................ | A61B 5/682 607/54 |
| 2011/0184558 A1 * | 7/2011 | Jacob | ................ | B25J 9/1689 901/47 |
| 2011/0190790 A1 * | 8/2011 | Summerer | ............. | A61B 34/76 606/130 |
| 2013/0178980 A1 * | 7/2013 | Chemouny | ............ | B25J 9/1671 700/255 |
| 2013/0211531 A1 * | 8/2013 | Steines | ................ | A61F 2/38 623/20.14 |
| 2013/0317369 A1 * | 11/2013 | Bryant-Greenwood | ..................... | G06T 5/007 382/128 |
| 2013/0345718 A1 * | 12/2013 | Crawford | ................ | A61B 34/76 606/130 |
| 2014/0058407 A1 * | 2/2014 | Tsekos | ................ | A61B 34/30 606/130 |
| 2014/0058755 A1 * | 2/2014 | Macoviak | ................ | G06Q 10/10 705/2 |
| 2014/0163368 A1 * | 6/2014 | Rousso | ................ | A61B 6/4258 600/436 |
| 2014/0180703 A1 * | 6/2014 | Mansker | ................ | G16H 30/00 705/2 |
| 2014/0188440 A1 * | 7/2014 | Donhowe | ................ | A61B 8/0841 703/1 |
| 2014/0222206 A1 * | 8/2014 | Mead | ................ | G02B 5/20 700/259 |
| 2014/0228644 A1 * | 8/2014 | Ikenaga | ................ | A61B 1/00193 600/166 |
| 2014/0264081 A1 * | 9/2014 | Walker | ................ | G01B 11/14 250/206.1 |
| 2014/0277726 A1 * | 9/2014 | Nakamura | ............. | B25J 9/1612 700/255 |
| 2014/0316436 A1 * | 10/2014 | Bar | ................ | A61B 90/50 901/9 |
| 2015/0025549 A1 * | 1/2015 | Kilroy | ................ | A61B 90/361 606/130 |
| 2015/0046137 A1 * | 2/2015 | Zeilinger | ................ | G16H 40/40 703/2 |
| 2015/0161331 A1 * | 6/2015 | Oleynik | ................ | G16H 10/60 705/3 |
| 2015/0190204 A1 * | 7/2015 | Popovi | ................ | A61B 6/4441 600/424 |
| 2015/0223832 A1 * | 8/2015 | Swaney | ................ | A61B 34/10 703/1 |
| 2015/0290454 A1 * | 10/2015 | Tyler | ................ | G06F 3/012 607/134 |
| 2015/0351860 A1 * | 12/2015 | Piron | ................ | A61B 5/0095 600/417 |
| 2015/0374446 A1 * | 12/2015 | Malackowski | ........ | A61B 34/32 606/130 |
| 2016/0000633 A1 * | 1/2016 | An | ................ | A61H 1/0277 601/33 |
| 2016/0361034 A1 * | 12/2016 | Hayashi | ................ | A61B 6/4014 |
| 2017/0020615 A1 * | 1/2017 | Koenig | ................ | A61B 34/72 |
| 2017/0197313 A1 * | 7/2017 | Nishino | ............. | A61B 5/02055 |
| 2017/0333137 A1 * | 11/2017 | Roessler | ................ | A61B 17/1703 |
| 2018/0001475 A1 * | 1/2018 | Steinle | ................ | A61B 90/37 |
| 2018/0014891 A1 * | 1/2018 | Krebs | ................ | A61B 17/15 |
| 2018/0071029 A1 * | 3/2018 | Srimohanarajah | ..... | A61B 90/37 |

(56) References Cited

U.S. PATENT DOCUMENTS

| | | | |
|---|---|---|---|
| 2018/0085175 A1* | 3/2018 | Steinle | G06T 11/001 |
| 2018/0092615 A1* | 4/2018 | Sakaguchi | A61B 5/02007 |
| 2018/0125591 A1* | 5/2018 | Camarillo | A61B 34/71 |
| 2018/0177383 A1* | 6/2018 | Noonan | A61B 1/0051 |
| 2018/0177556 A1* | 6/2018 | Noonan | A61B 34/10 |
| 2018/0211385 A1* | 7/2018 | Imai | G06T 7/0012 |
| 2018/0214005 A1* | 8/2018 | Ebata | A61B 5/02007 |
| 2018/0221240 A1* | 8/2018 | Yu | G09B 21/006 |
| 2018/0250352 A1* | 9/2018 | Conner | A61K 9/0019 |
| 2018/0289432 A1* | 10/2018 | Kostrzewski | A61B 34/30 |
| 2018/0295327 A1* | 10/2018 | Yearwood | B60P 3/025 |
| 2018/0325608 A1* | 11/2018 | Kang | A61B 34/20 |
| 2019/0000578 A1* | 1/2019 | Yu | A61B 34/10 |
| 2019/0005838 A1* | 1/2019 | Yu | G06F 3/011 |
| 2019/0005848 A1* | 1/2019 | Garcia Kilroy | G16H 40/67 |
| 2019/0090966 A1* | 3/2019 | Kang | A61B 17/1671 |
| 2019/0091864 A1* | 3/2019 | Matsudaira | G05B 19/416 |
| 2019/0125361 A1* | 5/2019 | Shelton, IV | A61B 90/30 |
| 2019/0125454 A1* | 5/2019 | Stokes | A61B 90/98 |
| 2019/0125455 A1* | 5/2019 | Shelton, IV | A61B 17/1155 |
| 2019/0125459 A1* | 5/2019 | Shelton, IV | A61B 90/30 |
| 2019/0133689 A1* | 5/2019 | Johnson | G09B 9/00 |
| 2019/0184198 A1* | 6/2019 | Mori | A61N 5/1064 |
| 2019/0201136 A1* | 7/2019 | Shelton, IV | A61B 17/0206 |
| 2019/0206562 A1* | 7/2019 | Shelton, IV | A61M 1/73 |
| 2019/0206565 A1* | 7/2019 | Shelton, IV | A61B 17/0682 |
| 2020/0100830 A1* | 4/2020 | Henderson | H04L 63/0227 |
| 2020/0118265 A1* | 4/2020 | Igarashi | A61B 5/7207 |
| 2020/0211713 A1* | 7/2020 | Shadforth | G06T 7/13 |
| 2020/0405403 A1* | 12/2020 | Shelton, IV | A61B 17/3417 |
| 2021/0158218 A1* | 5/2021 | Machida | G06N 3/0454 |
| 2021/0161588 A1* | 6/2021 | Fujisawa | G06T 11/203 |
| 2021/0169578 A1* | 6/2021 | Calloway | G06V 10/60 |
| 2021/0169605 A1* | 6/2021 | Calloway | A61B 90/36 |
| 2021/0275260 A1* | 9/2021 | Kang | A61B 34/76 |
| 2022/0028550 A1* | 1/2022 | Ng | G16H 30/20 |
| 2022/0104822 A1* | 4/2022 | Shelton, IV | A61B 90/98 |
| 2022/0233119 A1* | 7/2022 | Shelton, IV | A61B 17/07207 |
| 2022/0273291 A1* | 9/2022 | Shelton, IV | A61B 17/0686 |
| 2022/0344025 A1* | 10/2022 | Bort | A61B 5/256 |
| 2023/0029239 A1* | 1/2023 | Tsujimoto | A61B 1/0646 |
| 2023/0148847 A1* | 5/2023 | Gono | A61B 1/000094 600/101 |
| 2023/0165649 A1* | 6/2023 | Fitzsimons | A61B 34/30 700/245 |
| 2023/0180998 A1* | 6/2023 | Mizutani | G02B 23/24 600/101 |
| 2023/0190378 A1* | 6/2023 | Khurana | A61B 34/76 606/130 |
| 2023/0219231 A1* | 7/2023 | Okada | G06T 7/73 700/259 |
| 2023/0222666 A1* | 7/2023 | Takenouchi | G16H 30/20 382/128 |
| 2023/0225747 A1* | 7/2023 | Gogarty | A61B 17/1721 606/88 |
| 2023/0255442 A1* | 8/2023 | Masaki | A61B 1/00009 600/112 |
| 2023/0263581 A1* | 8/2023 | Forsyth | A61B 90/39 606/102 |
| 2023/0277259 A1* | 9/2023 | Kang | A61B 17/1671 606/130 |
| 2023/0329813 A1* | 10/2023 | Abbasi | A61B 34/10 |
| 2023/0363826 A1* | 11/2023 | Russell | A61B 34/30 |
| 2023/0380669 A1* | 11/2023 | Zhao | A61B 1/00149 |
| 2023/0380670 A1* | 11/2023 | Tavakkolmoghaddam | A61B 1/0016 |
| 2024/0025032 A1* | 1/2024 | López Del Pueyo | B25J 5/007 |
| 2024/0041549 A1* | 2/2024 | Tanimoto | A61B 90/03 |
| 2024/0081918 A1* | 3/2024 | Nishihara | A61B 34/20 |
| 2024/0081927 A1* | 3/2024 | Kodama | A61B 90/37 |
| 2024/0138941 A1* | 5/2024 | Zeng | A61B 34/74 |
| 2024/0180639 A1* | 6/2024 | Kang | A61B 34/10 |

FOREIGN PATENT DOCUMENTS

| | | | | |
|---|---|---|---|---|
| CN | 114631892 A | * | 6/2022 | |
| EP | 0335314 A2 | | 10/1989 | |
| EP | 1355765 A2 | | 10/2003 | |
| EP | 3212109 B1 | * | 1/2020 | A61B 34/10 |
| EP | 3414736 B1 | * | 8/2020 | |
| EP | 3628262 B1 | * | 3/2021 | A61B 34/10 |
| JP | 2009207677 A | * | 9/2009 | |
| JP | 2011217904 A | * | 11/2011 | |
| JP | 2020156800 A | * | 10/2020 | A61B 1/00006 |
| JP | 2021509332 A | * | 3/2021 | |
| JP | 2021509507 A | * | 3/2021 | |
| KR | 20210104190 A | * | 8/2021 | |
| WO | 02/060653 A2 | | 8/2002 | |
| WO | 2006075331 A2 | | 7/2006 | |
| WO | 2008130355 A1 | | 10/2008 | |
| WO | 2010140074 A1 | | 12/2010 | |
| WO | WO-2013018983 A1 | * | 2/2013 | A61B 34/30 |
| WO | WO-2014008929 A1 | * | 1/2014 | B25J 9/1666 |
| WO | 2015087335 A1 | | 6/2015 | |
| WO | WO 2018/050207 A1 | * | 3/2018 | |
| WO | WO-2020236937 A1 | * | 11/2020 | A61B 34/10 |

OTHER PUBLICATIONS

"A Perspective on Medical Robotics;" R.H. Taylor; Proceedings of the IEEE (vol. 94, Issue: 9, pp. 1652-1664); Sep. 1, 2006.*
European Patent Office, International Search Report and Written Opinion from corresponding International Application No., PCT/EP2015/075427, mail date, Jun. 7, 2016, 1-11pages.
Lasser, Michael S., et al., "Dedicated robotics team reduces pre-surgical preparation time", Indian Journal of Urology, (2012), vol. 28, Issue 3, pp. 263-266.
Chaumette, Francois, et al., "Visual servo control, Part I: Basic approaches", IEEE Robotics and Automation Magazine, Institute of Electrical and Electronics Engineers, (2006), 13 (4), pp. 82-90.
Office Action for corresponding European Application No. 19202230.9, dated Jan. 7, 2020. 4 Pages.

* cited by examiner

| treatment information data | constraint information data | spatial constraint data | priority |
| --- | --- | --- | --- |
| head surgery | person = surgeon | (X1, Y1, Z1), (Lx1, Ly1, Lz1), (α1, β1, γ1) | 1 |
| | person = nurse | (X2, Y2, Z2), (Lx2, Ly2, Lz2), (α2, β2, γ2) | 2 |
| | person = anesthetist | (X3, Y3, Z3), (Lx3, Ly3, Lz3), (α3, β3, γ3) | 3 |
| | equipment = OR table | (X4, Y4, Z4), (Lx4, Ly4, Lz4), (α4, β4, γ4) | 1 |
| | equipment = sterile barrier | (X5, Y5, Z5), (Lx5, Ly5, Lz5), (α5, β5, γ5) | 1 |
| | equipment = imaging device | (X6, Y6, Z6), (Lx6, Ly6, Lz6), (α6, β6, γ6) | 1 |

DETERMINING A CONFIGURATION OF A MEDICAL ROBOTIC ARM

RELATED APPLICATION DATA

This application is a national phase application of International Application No. PCT/EP2015/075427 filed Nov. 2, 2015, published in the English language, which claims benefit of International Application No. PCT/EP2015/070153 filed Sep. 3, 2015 and International Application No. PCT/EP2015/069037 filed Aug. 19, 2015.

TECHNICAL FIELD

The present invention relates to a computer implemented method for determining a configuration of a medical robotic arm and to a corresponding computer program and system.

SUMMARY

Many surgical procedures involve using a medical robotic arm, for example for carrying an instrument or an implant. A robotic arm typically has a base which is placed a particular position. The robotic arm can act in a certain work space relative to its base, wherein the work space depends on the structure of the robotic arm. A robotic arm typically comprises a plurality of arm segments, wherein two arm segments are connected via one or more joints. The entirety of all joint positions is referred to as the pose of the robotic arm. The position of the free end of the robotic arm within the work space thus depends on the pose of the robotic arm. The configuration of the robotic arm comprises the pose of the robotic arm and the position of the base of the robotic arm.

The performance of the robotic arm might be deteriorated in border areas of the work space. It might not be possible to reach some positions in the work space if the robotic arm carries a heavy load and the positioning accuracy of the robotic arm might be reduced in a border area. Depending on the intended use of the robotic arm, which for example comprises the weight of the load to be carried by the robotic arm or the required accuracy, the usable work space might be smaller than the maximum achievable work space of the robotic arm.

Space might be a limited resource during a surgical procedure, depending on the number of persons involved in the surgical procedure and hardware used in the surgical procedure. It is thus an object of the present invention to find the configuration of a medical robotic arm, such as a configuration heaving the smallest possible impact on the freedom of the persons involved in the surgical procedure. The configuration can be an initial configuration, which is a configuration of the robotic arm at the beginning of the surgical procedure. Before assuming this initial configuration, the robotic arm can have another configuration, for example if the base of the robotic arm is placed in a free space of the operating room. In another case, the configuration can be a configuration during the surgical procedure.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention relates to a computer implemented method for determining a configuration of a medical robotic arm, wherein the configuration comprises a pose of the robotic arm and a position of a base of the robotic arm. The method comprises the step of acquiring treatment information data representing information about the treatment to be performed by use of the robotic arm. The method further comprises the step of acquiring patient position data representing the position of a patient to be treated. The method still further comprises the step of calculating the configuration from the treatment information data and the patient position data.

An end-effector, such as a fine-tuning unit or a hand-like unit, could be attached to the end of the robotic arm. In this case, the configuration of the robotic arm optionally further comprises the configuration of the end-effector.

The position of the patient, the position of the base of the robotic arm and areas or positions mentioned elsewhere in this document are preferably given with respect to the same reference, which can be a coordinate system defined with respect to an operating room. A position is typically defined in up to three translational dimensions and up to three rotational dimensions, and thus defines a location and an alignment.

In one embodiment, the treatment information data comprises information regarding at least one of a disease to be treated, a body part to be treated and a medical procedure to be performed on the patient. The disease might be identified according to the International Classification of Diseases (ICD).

The information regarding a disease to be treated might further include the location within the patient's body to be treated, regions of interest (ROI), organs at risk or any other diagnostic information or information obtained from an electronic health record (EHR) of the patient, a Hospital Information System (HIS) or a Picture Archiving and Communication System (PACS). A PACS can provide image data, which might add anatomical information like distance, size or shape of objects or organs.

The treatment information data in combination with the patient position data define a desired area in space which shall be accessible by the robotic arm, and is also referred to as required work space. The configuration is calculated from those data such that the robotic arm can reach this desired area. Calculating the configuration can make use of a model which describes the robotic arm in terms of possible joint positions and supportable loads.

In one embodiment, a plurality of hypothetical base positions are tested. A hypothetical base position is selected, the reachable work space is determined for this base position and the reachable work space is compared to the required work space.

The patient position data may represent the position of the patient directly or indirectly. A direct representation can include the position of a patient, or the body parts to be treated, in up to six dimensions. An indirect representation may for example include the position of an operating room table in combination with an assumption on how the patient is positioned on the operating room table.

The treatment information data may further comprise patient information data representing information about the patient to be treated. This information may for example involve the sex, the weight, the body height or the BMI of the patient. The required work space for example depends on the patient information data.

The treatment information data may further comprise imaging data representing raw or processed images of the patient. It might for example comprise a CT image, an MR image, information from fused image data sets, segmented objects or atlas based information or anatomical information (like dimension, size or shape of objects or organs) derived from the images. The required work space for example depends on the imaging data and/or the anatomical information derived therefrom.

In one embodiment, the method further comprises the step of acquiring constraint information data and the step of transforming the constraint information data into spatial constraint data representing spatial constraints for the configuration of the robotic arm. In this embodiment, the calculation of the configuration is further based on the spatial constraint data.

The constraint information data represents at least one of people data describing people involved in the treatment, equipment data describing equipment used for the treatment other than the robotic arm, room data describing the room in which the treatment is performed and robot data describing properties of the robotic arm.

The people data may identify the number of persons involved in the treatment and optionally the preferences, the department and the profession of an involved person. Typically, involved persons may include the surgeon, a scrub nurse, an anesthetist, a technician and a visitor. Each person involved in the treatment requires a particular area in space with which the robotic arm should not interfere. A visitor can have an assigned spectator area, which is known to the algorithm.

The equipment described by the equipment data may for example comprise an operating room table having a type, configuration and/or layout, imaging devices (for example defined by their types, geometries and/or live position), treatment devices such as treatment beam generators, or other equipment, such as for example a sterile barrier, devices for anesthesia or holding devices for holding an object. Imaging devices can be of any kind, including ultrasound imaging devices, microscopes or endoscopes.

The room data describes properties of the room in which the treatment is to be performed. It might include at least one of the room number, the geometry of the room, information of fixed installations in the room, such as booms or lights, information on equipment flow, information on sterile tables and information on air flow within the room. The equipment flow describes the movement of equipment over time, for example for different workflow steps. Sterile tables define areas which must not be entered by the (non-sterile) robotic arm.

The robot data may comprise information on at least one of the type, the size, the degrees of freedom, the footprint or the maximum payload of the robot. In addition or as an alternative, it may involve information about start positions, movement options or the current state of the robot.

The spatial constraint data does for example represent the spatial constraints in terms of areas in space into which the robotic arm should not enter. Such an area might have an associated priority, such that the robotic arm can enter areas with lower priorities if it is not possible to fulfill all spatial constraints.

In one embodiment, transforming the constraint information data involves retrieving the spatial constraint data corresponding to the constraint information data from a database. The word "database" includes all possible sources which can assign spatial constraint data to constraint information data.

In one embodiment, the method determines the spatial constraints corresponding to all provided constraint information data and combines them to an overall spatial constraint which describes an area into which the robotic arm should not intrude. The configuration is then calculated such that this criterion is met. Preferably, the base of the robotic arm is positioned outside the area described by the overall spatial constraint.

The method may further comprise a step of acquiring live data, wherein the calculation of the configuration is further based on the live data.

The live data may comprise sensor data, such as data representing a torque, a force, a speed or an acceleration of or exerted onto the robotic arm or a part of the robotic arm. This may further comprise gravity data or gyroscope data. In addition, it can comprise imaging data, such as images output from cameras, medical imaging devices or ultrasound devices. It may further comprise position data of objects, such as objects within a predetermined distance from the base of the robotic arm. The position data can for example be determined by a medical navigation or tracking system.

Cameras could monitor the movement of the OR table, a scanner, imaging devices, treatment devices or persons in the room to generate the live data. Ultrasound devices could monitor the proximity of the robot for collision detection and/or avoidance with equipment, the patient and/or other people. Cameras could recognize a new workflow step, for example by pattern recognition or recognition of an instrument specific UDI (unique device identifier) code.

Touching the robotic arm, which hosts force or acceleration sensors, could lead to new situations and/or necessary new configurations. Touching the robotic arm can occur in an intentional way, for example by moving and/or guiding the robot or stopping the robot, or in an unintentional way, for example by suddenly getting in its way, such that robot performs a security stop.

In one embodiment, the pose of the configuration is a generic default pose. This means that the method only calculates the position of the base of the robotic arm. The default pose may be a central pose in which the free end of the robotic arm is in the center of the work space.

In one embodiment, the pose of the robotic arm is calculated such that it is an optimum starting point from which all poses of the robotic arm required during the treatment can be reached with the best possible performance of the robotic arm.

In one embodiment, the configuration of the medical robotic arm further comprises work space data representing a limited work space which the robotic arm is allowed to occupy. This limits the movement of the robotic arm to the limited work space, which imposes a limitation to the allowed joint positions. On the other hand, the robotic arm is not allowed to enter the space outside the limited work space. The limited work space and the area described by the overall spatial constraint do for example not overlap.

The present invention further relates to a computer implemented method for determining the configuration of a medical robotic arm, wherein the configuration comprises a pose of a robotic arm and a position of a base of the robotic arm. The method comprises the step of acquiring changed environment data representing a change in the environment in which the robotic arm is used and the step of calculating the configuration of the robotic arm from the changed environment data. The reference environment compared to which the changed environment data is defined is for example the environment for which the current configuration of the robotic arm was calculated.

If the environment of the robotic arm changes, it might be advantageous to adapt the configuration of the medical robotic arm accordingly.

In one embodiment, the changed environment data is acquired by a medical tracking system and includes the position of an object tracked by the medical tracking system. The method is thus aware of the current position of the object and can adapt the configuration of the robotic arm accordingly. The method preferably knows or acquires the size of the object. The method can calculate spatial constraint data representing spatial constraints caused by the position of the object, wherein the calculation of the configuration is further based on this spatial constraint data.

The changed environment data can include information about the beginning of a new workflow step of a workflow which uses the robotic arm. Each workflow step can have associated positions of people involved in the treatment, information about equipment used in the workflow step, including the position of the equipment, and tasks to be performed in the workflow step. This may lead to workflow step constraint information data, which is constraint information data associated with the workflow step. The calculation of the robotic arm is then based on the workflow step spatial constraint data.

The changed environment information may include movement data representing the movement of a device other than the robotic arm. During the treatment, a device might move. Common examples are treatment beam generators or imaging devices which for example move along the inferior-superior axis of the patient and/or around the inferior-superior axis of the patient. The movement of the device is typically controlled by a control unit, such that information about the movement is known and can be provided to the method. In addition or alternatively, the movement can be tracked. The movement data can for example be used for updating the constraint information data. The changed environment information may be derived from the live data which have been explained above.

In one embodiment, the method further comprises the step of acquiring patient position data representing the position of a patient to be treated. In this embodiment, the calculation of the configuration of the robotic arm is further based on the patient position data.

In one embodiment, the method further comprises the step of acquiring constraint information data and the step of transforming the constraint information data into spatial constraint data representing spatial constraints for the configuration of the robotic arm. In this embodiment, the calculation of the configuration is further based on the spatial constraint data. Details of this embodiment and the constraint information data are the same as explained above.

In one embodiment, the configuration of the medical robotic arm further comprises work space data representing a limited work space which the robotic arm is allowed to occupy. Details of this embodiment are the same as explained above.

In one embodiment, the method further comprises the step of acquiring a current configuration of the robotic arm, wherein the current configuration of the robotic arm is used as the configuration of the robotic arm if the current configuration of the robotic arm does not interfere with the changed environment. In other words, it is determined whether or not the current configuration of the robotic arm is also suitable for the changed environment. If this is the case, the configuration of the robotic arm does not have to be changed.

In one embodiment, the method further comprises the step of outputting configuration change data which represents a change to be performed on the current configuration of the robotic arm to obtain a desired configuration of the robotic arm. This may for example involve outputting a target position of the base of the robotic arm, for example to a human who can move the base of the robotic arm or to an automatic positioning system. It may further involve outputting the target pose, and optionally the target configuration of an end-effector, to the robotic arm, for example to a controller which controls the robotic arm, or to a user who manipulates the robotic arm.

The present invention also involves applying the calculated configuration of the robotic arm, which means to bring the robotic arm into the calculated configuration. It for example involves moving the base of the robotic arm to the calculated position.

The present invention further relates to a program which, when running on a computer, causes the computer to perform the method steps of at least one of the methods described above and/or a program storage medium on which the program is stored, in particular in a non-transitory form.

The present invention further relates to a system for determining a configuration of a medical robotic arm, the system comprising a computer on which the aforementioned program is stored and/or run.

The present invention has the technical effect that an ideal set-up for the robotic arm and an optimized workflow of the robotic procedure can be obtained.

The needed space is minimized and/or the use of available space is optimized. For example, the robotic arm uses a position where it uses space which is otherwise not needed, e.g. in the very corner between an imaging device and the OR table hosting the patient.

Interference with the user, staff, anesthesia and patient is minimized. All medical professionals can perform their duties completely without or with only minimal interference with the robotic arm. Tools like drills can still be used in the intended way, but with minimal or no compromises for the patient set-up, such as arm positions.

Collisions with other equipment like imaging devices, OR lights, air flow cabinets, sterile tables, including moving equipment, such as an OR table changing its height or an imaging device performing a scan, can be avoided.

In addition, collisions with already performed surgical steps, for example with a used instrument or an implant (e.g., an already implanted needle, catheter, electrode or the like) can be avoided since corresponding information will be considered in future movements and positions of the robotic arm.

The present invention allows for maximum flexibility of robotic movements, with the robotic arm having a maximum of options to move to any new desired position. This means the best possible position during performance of a robotic task with respect to payload, stability and rigidity of the robot.

In addition, the risk of breaking the sterile barrier is minimized.

Definitions

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital light-box. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

The present invention can be used for any robotic solution, for example for neurosurgical, spinal, or further procedures, which imply the use of a robotic arm and optionally an end-effector. Examples are stereotactic procedures like biopsies, DBS, SEEG, or Shunts or spinal procedures like k-wires, pedicle screws, pain management or biopsies. The invention improves set-up and workflow when using a robotic solution, automatically proposing and/or defining an ideal configuration and/or adapting and changing this optimal configuration over time, for example when constraints change, new workflow steps start, etc. The procedure becomes faster, more intuitive, less error prone, less tiresome or less shaky and has improved repeatability.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
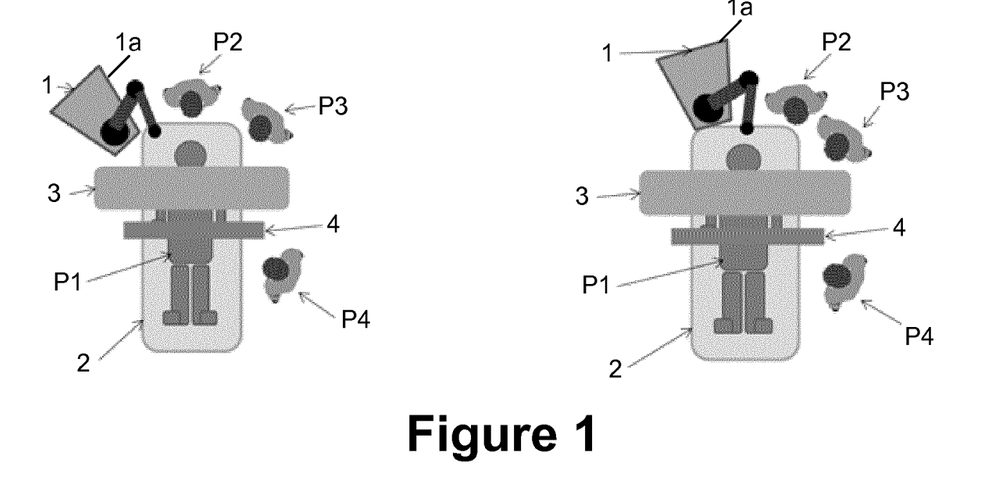
FIG. 1 two different configurations of a robotic arm.

FIG. 1 shows two configurations of a robotic arm 1 in an exemplary scenario. This scenario relates to a head surgery, wherein a head of a patient P1 is to be treated. The patient P1 is lying on an operating room table 2. Involved in the treatment is a surgeon P2, a nurse P3 and an anesthetist P4. Further provided is an imaging unit 3, which is for example an MR imaging unit, and a sterile barrier 4, which separates a sterile area from a non-sterile area.

The medical robotic arm 1 comprises a base 1a and a plurality of segments, wherein two adjacent segments are connected via at least one joint. One end is attached to the base 1a, for example via at least one joint, and the other end, which is also referred to as a free end, can move in space depending on the joint positions, which represent the positions of the joints between the segments and is also referred to as pose of the robotic arm 1. The combination of the pose of the robotic arm and the position of the base 1a of the robotic arm is called the configuration of the robotic arm 1.

Each of the persons P2 to P4 involved in the treatment and of the equipment (imaging device 3 and sterile barrier 4) requires a particular spatial area during the treatment. The required areas may vary for different workflow steps of the treatment. It is therefore essential to determine a suitable configuration of the robotic arm 1, in particular a proper position of the base 1a of the robotic arm 1. The configuration of the robotic arm 1 might be different for two or more different workflow steps, but could also be the same for all workflow steps.

The left and right parts of FIG. 1 show different positions of the base 1a of the robotic arm 1, and therefore different configurations of the robotic arm 1. For the configuration shown in the left part of FIG. 1, the position of the base 1a of the robotic arm 1 is such that all persons and parts of the equipment have enough room for performing the treatment. For the position of the base 1a of the robotic arm 1 shown in the right part of FIG. 1, to the contrary, the freedom of the surgeon P2 and the nurse P3 is limited by the robotic arm 1, which can easily lead to deteriorated results of the treatment. The configuration of the robotic arm 1 in the left part of FIG. 1 is therefore favorable over the configuration of the robotic arm 1 shown in the right part of FIG. 1.

Figure 2:
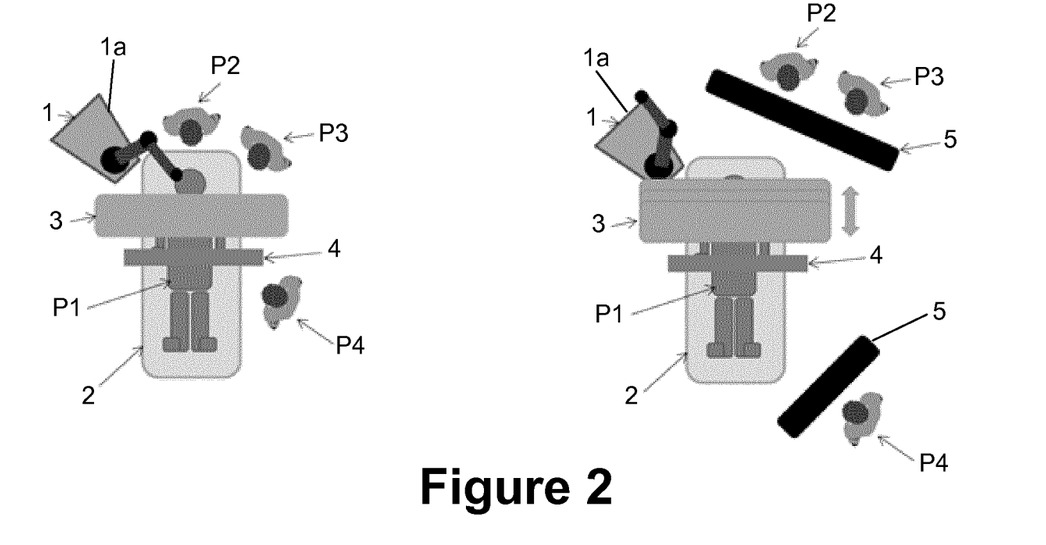
FIG. 2 a scenario in which the present invention is used.

FIG. 2 shows scenarios similar to the one shown in FIG. 1 for two different workflow steps of a treatment of the patient P1. In the workflow step shown in the left part of FIG. 1, the free end of the robotic arm 1a is near the head of the patient P1, for example for holding a medical instrument or a medical tool.

In the workflow step shown in the right part of FIG. 2, the free end of the robotic arm 1 is retracted and the imaging device 3 is being used for imaging the head of the patient P1. During the imaging process, the imaging device 3 moves along the inferior-superior axis of the patient P1 as indicated by the double arrow. Since the imaging device 3 emits x-ray radiation during the imaging process, the persons P2 to P4 are standing behind protective shields 5.

Figure 3:
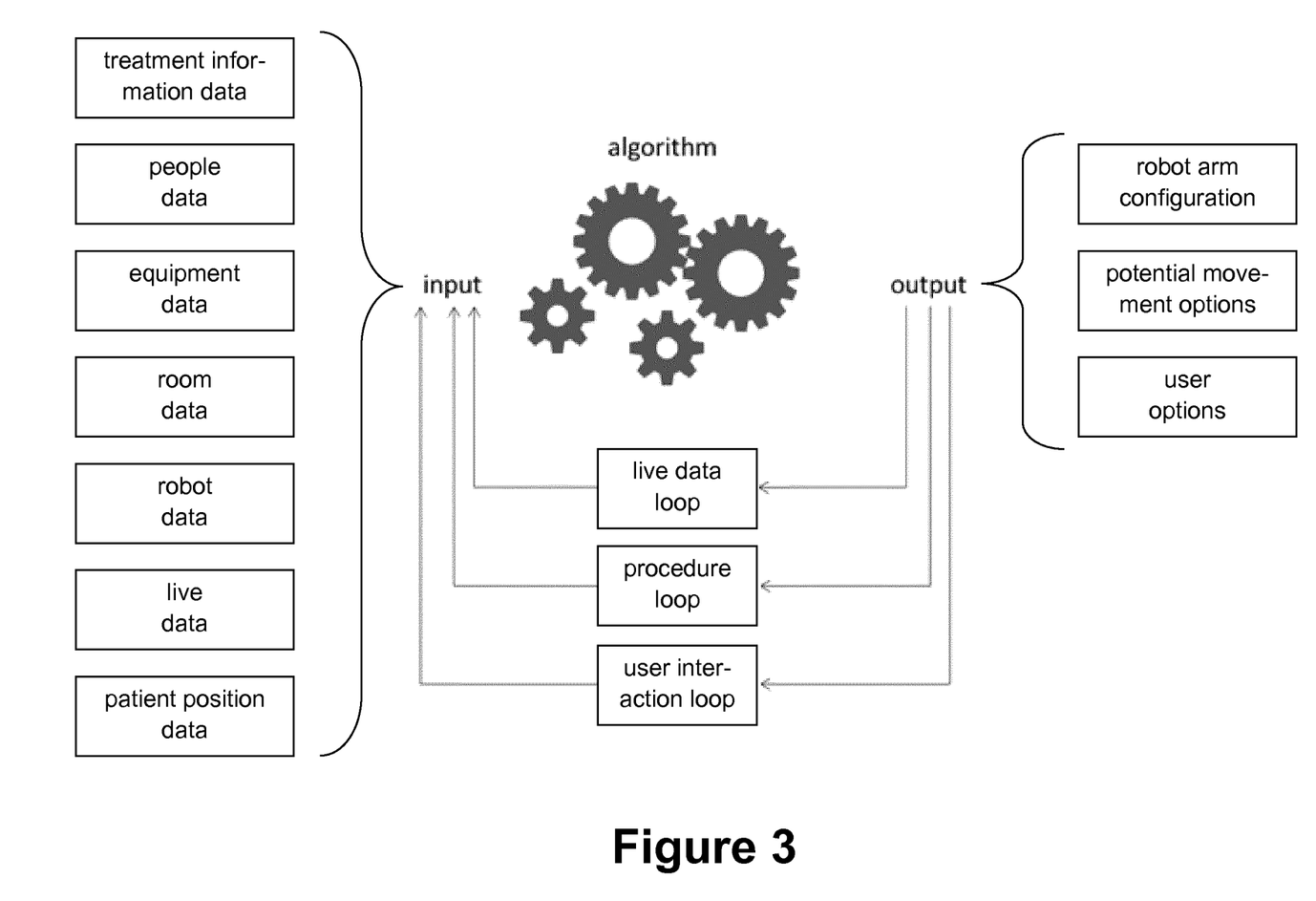
FIG. 3 a schematic overview of the present invention.

FIG. 3 gives a schematic overview of the data which are processed and output by the algorithm for calculating the configuration of the robotic arm 1 according to the present invention.

On the input side, there are treatment information data, people data, equipment data, room data, robot data, live data and patient position data. The people data, equipment data, room data and robot data can be summarized as constraint information data. They define spatial constraints on the configurations of the robotic arm 1. The constraint information data are optional, but advantageous.

The treatment information data comprises at least one of the diagnosis, the disease, disease classification, diagnostic information, location of the treatment, regions of interest, organs at risk, medical images and processed images.

The people data comprises information on at least one person involved in the treatment, such as the patient, a surgeon, a scrub-nurse, and an anesthetist, including the department, profession and personal preferences of the person. Patient data might include patient weight (which might cause potential bending of the OR table), patient position (for example prone versus supine versus lateral) or equipment effecting patient access (such as cables, tubes, stickers or holders).

The equipment data comprises at least one of the operating room table type, layout, height, operating room lights, devices for anesthesia, imaging devices, treatment devices and tools used for the treatment.

The room data comprises at least one of room number, room geometries, fixed installations, such as booms or lights, equipment flow, sterile tables or air flow.

The robot data comprises at least one of type, size, footprint, maximum payload, work space, start options, movement options, and current state of the robotic arm 1. Start options might indicate a possible initial position like a park position, a position in the middle of the treatment volume or a position in the middle of the achievable work space of the robot (avoiding border positions which affect maximum load and/or accuracy).

Live data comprises data from sensors, such as torque, force, speed, acceleration, gravity and gyroscopic information, and from other devices such as imaging devices and orientation devices, like cameras or ultrasound devices.

The patient position data represent the position of the patient P1 to be treated.

The treatment information data basically describes the part of the patient P1 to be treated, for example relative to a patient coordinate system. Since the position of the patient P1 is known from the patient position data, which defines the position of the patient in space relative to a reference, such as a reference system associated with the operating room, the spatial area to be treated is known or can be calculated in this reference system. The patient position data may derived from the treatment information data and the position of the operating room table 2 in the reference system, for example if the position of the patient P1 on the operating room table 2 is known or can be estimated.

The output of the algorithm comprises the configuration of the robotic arm 1. Optional outputs are potential movement data and/or user options data. As mentioned above, the configuration comprises a pose of the robotic arm 1 and a position of the base of 1a of the robotic arm 1. However, the pose of the robotic arm 1 might be a default pose, such that the algorithm only calculates the position of the base 1a of the robotic arm. User options could be a manual movement of the robot, for example if the robot has 7 degrees of freedom and there is a variety of possible configurations. Another user option could be that the robot builds a boundary box, in which all robot positions would be good, but the user can select (within the box) the final position. In this example, the algorithm allows a multitude of good or even ideal positions within the box. Another user option could be to either move the base or to move the arm to achieve the desired, good or ideal position or to combine the base position and the arm pose in a way to achieve the best configuration calculated by the algorithm.

The potential movement data describe potential movement options that minimize interference of the robotic arm 1 with the patient P1 other persons P2 to P4, equipment 3 and 4 and further procedure steps of the treatment. They do for example describe the transition from one pose to another. A controller of the robotic arm 1 is then not free to determine the transition, because this could lead to a violation of a constrained space. The transition is instead provided to the controller.

The overview of FIG. 3 further comprises different loops connecting the output of the algorithm to the input of the algorithm. The first loop is the live data loop, which provides updated live data to the algorithm.

A second loop is a procedure loop which indicates changed environment data to the algorithm. The changed environment data represents a change in the environment in which the robotic arm 1 is used. This may comprise at least one of information on already performed workflow steps of the treatment, new layouts, new positions of persons or equipment involved in the treatment and other constraints. New layouts can refer to potential repositioning of the patient during the surgical procedure, leading to a new layout of the surgery. In an abdominal case for example, access could be first through ports in the stomach wall, whereas later on access is through the colon. New layouts can further describe how equipment could be moved to a new position or could be removed as it is not needed anymore, leading to increased space for the robot. New layouts can still further describe that an additional surgeon enters the procedure for a later and/or more complex step, The user interaction loop provides user interaction data to the algorithm. The user interaction data may comprise at least one of options selected by the user, options confirmed by a user or information indicating that the user ignores or overrides the calculated configuration of the robotic arm 1. The user could for example use the advantage of a robot with 7 degrees of freedom to select the best option in case more than one option exists, could consider constraints not present in the algorithm or could react to unforeseen situations, complications or life threatening conditions, for example by abandoning the case, removing the robot, changing the planned treatment or adding new unknown equipment.

With the feedback loops described above, it is possible to update a configuration of the robotic arm 1 depending on any changes occurring in the environment or the scenario in which the robotic arm 1 is used.

The present invention also involves to bring the robotic arm 1 into the calculated configuration, for example by relocating the base 1a of the robotic arm 1 or providing the configuration to a controller of the robotic arm 1, which controls the robotic arm 1 to assume the pose comprised in the configuration.

Figure 4:
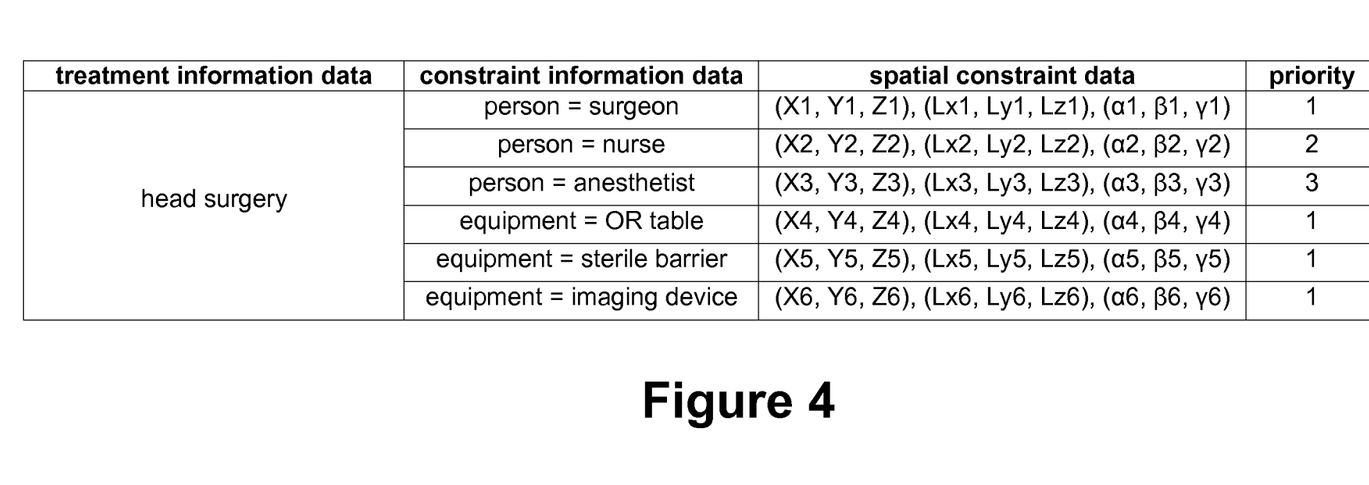
FIG. 4 a table comprising spatial constraint data and
FIG. 5 a system according to the present invention.

FIG. 4 shows a table which comprises spatial constraint data for the configuration of the robotic arm 1 depending on treatment information data and constraint information data.

FIG. 4 also assigns a priority to each spatial constraint data item. FIG. 4 only shows a part of the whole table.

In the example shown in FIG. 4, the treatment information data indicates a head surgery. For the head surgery, the table comprises a plurality of entries for different constraint information data. Spatial constraint data and a priority are assigned to each item of the constraint information data. In the present embodiment, the spatial constraint data describe a cuboid defined by a position, which is given by three coordinates (X, Y, Z), an orientation, which is given three angles ($\alpha$, $\beta$, $\gamma$), and a size given by three length values (Lx, Ly, Lz). However, the spatial constraint data may describe a spatial area of any other shape and/or by any other suitable parameters.

In the table, different spatial constraint data are defined for a surgeon, a nurse and an anesthetist. In addition, spatial constraint data are defined for an operating room table, a sterile barrier and an imaging device.

Figure 5:
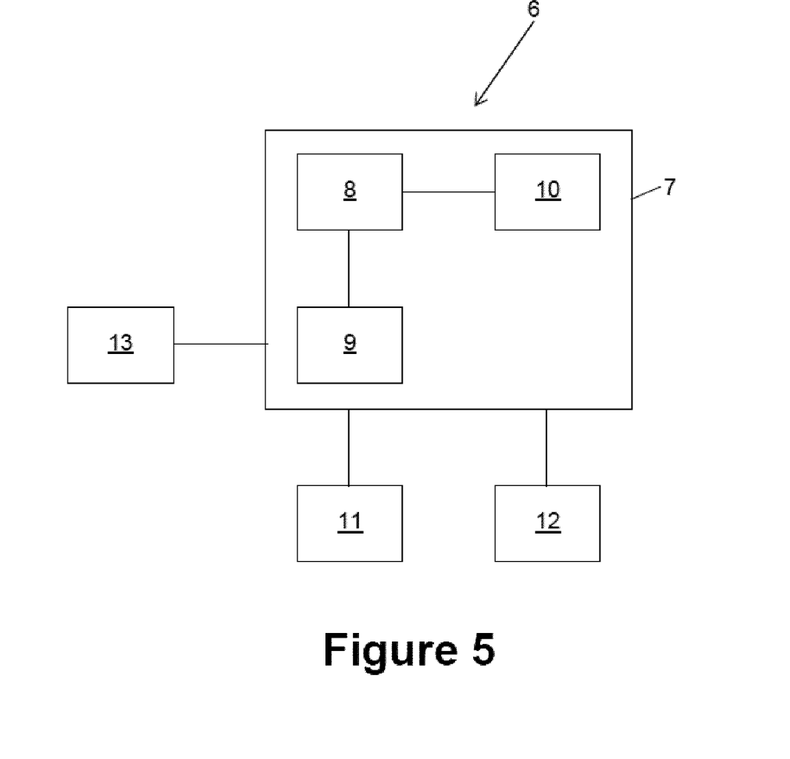

FIG. 5 schematically shows a system 6 for carrying out the present invention. The system 6 comprises a computer 7 connected to an input unit 11 and an output unit 12. The input unit 11 can be any suitable input unit, such a mouse, a keyboard, a touch screen or any other man-machine interface. The output unit 12 can be any suitable output unit such as a monitor or a projector.

The computer 7 comprises a central processing unit 8 connected to an interface 9 and a memory unit 10. Via the interface 9, the central processing unit 8 can acquire data, such as the treatment information data, the constraint information data and the live data. The memory unit 10 can store working data, such as the acquired data, and program data which implements the method according to the present invention.

In one embodiment, the central processing unit 8 acquires all available input data, such as the treatment information data, the patient position data and constraint information data. The central processing unit 8 then accesses a table like the one shown in FIG. 4 to determine spatial constraint data and corresponding priorities depending on the treatment information data and the constraint information data. The central processing unit 8 then combines the obtained spatial constraint data to calculate an overall spatial area into which the robotic arm 1 shall not enter. The central processing unit 8 then calculates the configuration of the robotic arm 1 from the treatment information data, the patient position data and the combined spatial area into which the robotic arm 1 shall not enter.

If there is no suitable configuration for the robotic arm 1 under the given conditions, the central processing unit 8 repeats the process of calculating the configuration, but ignores one or more spatial constraint data with the lowest priority.

In another embodiment, the central processing unit 8 acquires changed environment data. In the present example, the changed environments data indicates a workflow step or a change in the workflow step, such as from the workflow step shown in the left part of FIG. 2 to the workflow step shown in the right part of FIG. 2, and live data. The changed environment data indicates that the imaging unit 3 is used for imaging the head of the patient P1, which includes a movement of an imaging device 3 along the inferior-superior axis of the patient P1. This implies changed spatial constraint data corresponding to the imaging device 3, such that the configuration of the robotic arm 1 is to be updated.

The central processing unit 8 calculates the (updated) configuration of the robotic arm 1 from the changed environment data. The calculation can further be based on at least one of constraint information data, patient position data and the current configuration of the robotic arm. In the example shown in FIG. 2, the position of the base of the robotic arm 1 can be maintained, while the pose of the robotic arm 1 has to be changed in order to free the space required for the movement of the imaging device 3.

Further examples include that the changed environment data indicates changes in the constraint information data. The computer 7 is connected to a medical tracking system 13 via the interface 9. The medical tracking system 13 then tracks the position of an object, for example by detecting a marker device attached to the object. If it detects a change in the position of the object, it generates corresponding changed environment data which is acquired by the central processing unit 8 and used for calculating the configuration of the robotic arm 1.

The invention claimed is:

1. A computer implemented method for determining a configuration of a medical robotic arm, the configuration of the medical robotic arm comprising a pose of the medical robotic arm and a position of a base of the medical robotic arm, the method comprising:
    detecting, based on live data captured from the environment, a change in the environment and acquiring changed environment data describing at least a change in positions of persons or a change in equipment, wherein the changed environment data being indicative of a workflow step for a workflow which uses the medical robotic arm and wherein the workflow includes a plurality of workflow steps;
    acquiring constraint information data associated with the workflow step based on the changed environment data and the live data, wherein respective constraint information is assigned to each workflow step of the workflow, and wherein the constraint information includes one or more of: (i) people data describing positions of persons involved in a treatment, (ii) equipment data describing equipment used for the treatment other than the medical robotic arm, (iii) room data describing a room in which the treatment is performed, and (iv) robot data describing properties of the medical robotic arm;
    transforming the constraint information data into spatial constraint data, the spatial constraint data representing space in which the medical robotic arm is constrained for the workflow step; and
    determining the configuration of the medical robotic arm for the workflow step based on the spatial constraint data.

2. The method of claim 1, further comprising acquiring patient position data representing a position of an associated patient, wherein the calculation of the configuration of the medical robotic arm is further based on the patient position data.

3. The method of claim 1, further comprising acquiring a current configuration of the medical robotic arm, wherein the current configuration of the medical robotic arm is used as the configuration of the medical robotic arm when the current configuration of the medical robotic arm does not interfere with the change in the environment.

4. The method of claim 1, wherein the changed environment data is acquired from a medical tracking system and includes the position of an object tracked by the medical tracking system.

5. The method of claim 1, wherein the changed environment data includes movement data representing a movement of a device other than the medical robotic arm.

6. The method of claim 1, wherein the configuration of the medical robotic arm further comprises work space data representing a work space that the medical robotic arm is allowed to occupy.

7. The method according to claim 1, further comprising:
acquiring treatment information data representing information about a treatment to be performed on an associated patient by use of the medical robotic arm,
wherein the calculating the configuration of the medical robotic arm is further based on the treatment information data.

8. The method of claim 1, further comprising controlling the medical robotic arm in accordance with the configuration in response to the indicated beginning of the workflow step.

9. A non-transitory computer readable storage medium storing a program for determining a configuration of a medical robotic arm, the configuration of the medical robotic arm comprising a pose of the medical robotic arm and a position of a base of the medical robotic arm, the computer program, which, when running on a computer, or loaded onto the computer, causes the computer to:
detect, based on live data captured from the environment, a change in the environment and acquire changed environment data describing at least a change in positions of persons or a change in equipment, wherein the changed environment data being indicative of a workflow step for a workflow which uses the medial robotic arm and wherein the workflow includes a plurality of workflow steps;
acquire constraint information data associated with the workflow step based on the changed environment data and the live data, wherein respective constraint information is assigned to each workflow step of the workflow, and wherein the constraint information includes one or more of: (i) people data describing positions of persons involved in a treatment, (ii) equipment data describing equipment used for the treatment other than the medical robotic arm, (iii) room data describing a room in which the treatment is performed, and (iv) robot data describing properties of the medical robotic arm;
transform the constraint information data into spatial constraint data, the spatial constraint data representing space in which the medical robotic arm is constrained for the workflow step; and
determine the configuration of the medical robotic arm for the workflow step based on the spatial constraint data.

10. The non-transitory computer readable storage medium of claim 9, the program further causing the computer to control the medical robotic arm in accordance with the configuration in response to the indicated beginning of the workflow step.

11. A system for determining a configuration of a medical robotic arm, the configuration of the medical robotic arm comprising a pose of the medical robotic arm and a position of a base of the medical robotic arm, the system comprising:
a medical robotic arm; and
a computer configured to:
detect, based on live data captured from an environment, a change in the environment and acquire changed environment data describing at least a change in positions of persons or a change in equipment, wherein the changed environment data being indicative of a workflow step for a workflow which uses the medical robotic arm and wherein the workflow includes a plurality of workflow steps;
acquire constraint information data associated with the workflow step based on the changed environment data and the live data, wherein respective constraint information is assigned to each workflow step of the workflow, and wherein the constraint information includes one or more of: (i) people data describing positions of persons involved in a treatment, (ii) equipment data describing equipment used for the treatment other than the medical robotic arm, (iii) room data describing a room in which the treatment is performed, and (iv) robot data describing properties of the medical robotic arm;
transform constraint information data into spatial constraint data, the spatial constraint data representing space in which the medical robotic arm is constrained for the workflow step; and
determine the configuration of the medical robotic arm for the workflow step based on the spatial constraint data.

12. The system according to claim 11, wherein the computer is further configured to acquire patient position data representing a position of an associated patient, wherein the calculation of the configuration of the medical robotic arm is further based on the patient position data.

13. The system according to claim 11, wherein the computer is further configured to acquire a current configuration of the medical robotic arm, wherein the current configuration of the medical robotic arm is used as the configuration of the medical robotic arm when the current configuration of the medical robotic arm does not interfere with the change in the environment.

14. The system according to claim 11, further comprising:
a medical tracking system,
wherein the changed environment data is acquired from the medical tracking system and includes the position of an object tracked by the medical tracking system.

15. The system according to claim 11, further comprising:
a device other than the medical robotic arm,
wherein the changed environment data includes movement data representing a movement of the device other than the medical robotic arm.

16. The system according to claim 11, wherein the configuration of the medical robotic arm further comprises work space data representing a work space that the medical robotic arm is allowed to occupy.

17. The system according to claim 11, wherein the position of the base of the medical robotic arm moves to a calculated position based on the calculated configuration of the medical robotic arm.

18. The system according to claim 11, wherein the computer is further configured to:
acquire treatment information data representing information about a treatment to be performed on an associated patient by use of the medical robotic arm, and
calculate the configuration of the medical robotic arm further based on the treatment information data.

19. The system of claim 11, wherein the computer is further configured to control the medical robotic arm in accordance with the configuration in response to the indicated beginning of the workflow step.

20. A computer implemented method for determining a configuration of a medical robotic arm, the configuration of the medical robotic arm comprising a pose of the medical robotic arm and a position of a base of the medical robotic arm, the method comprising:
acquiring treatment information data representing information indicating a medical procedure to be performed by use of the robotic arm and a disease to be treated, wherein the disease to be treated indicated within the treatment information data is identified by a particular disease classification of a plurality of disease classifications, wherein the treatment information indicates a workflow for the medical procedures including a plurality of workflow steps;

retrieving from a database which associates diseases to be treated with locations or regions within a patient's body, a location or region within a patient's body corresponding to the disease to be treated for respective workflow steps, wherein the location or region is defined with respect to the patient's body;

detecting, based on live data captured from the environment, a change in positions of persons or a change in equipment, the changes being indicative of a workflow step of the plurality of workflow steps;

transforming constraint information associated with the workflow step and the treatment information data, into spatial constraint data indicating space in which movement of the medical robotic arm is to be constrained;

retrieving a model that describes the robotic arm in terms of possible joint positions;

acquiring patient position data representing a position of the patient to be treated, wherein the patient position data defines the position of the patient relative to at least one reference point of both the physical environment of the user and the robot;

calculating a configuration that the medical robotic arm shall assume from the location or region within the patient's body corresponding to the workflow step and based upon the disease to be treated in the treatment information data, the patient position data, the spatial constraint data, and the model which describes the robotic arm such that the configuration is a starting point from which all poses of the robotic arm required during the treatment can be reached, wherein calculating the configuration includes ensuring positions to be reached by the free end of the robotic arm include the locations or regions within the patient's body corresponding to the workflow step and the disease to be treated, and further includes determining a position of the base, wherein the base is movable, and wherein the position of the base is determined relative to the at least one reference point of the physical environment of both the user and the robot; and providing control signals to a controller of the robotic arm based upon the calculated configuration allowing the robotic arm to assume a pose defined by the calculated configuration.

* * * * *